United States Patent
Yun et al.

(10) Patent No.: US 7,875,295 B2
(45) Date of Patent: Jan. 25, 2011

(54) PROCESS FOR THE CONTROLLED PRODUCTION OF ORGANIC PARTICLES

(75) Inventors: Sung Lai Jimmy Yun, Faber Heights (SG); Jian Feng Chen, Singapore (SG)

(73) Assignee: Nanomaterials Technology Pte Ltd, Ayer Rajah Cresc (SG)

( * ) Notice: Subject to any disclaimer, the term of this patent is extended or adjusted under 35 U.S.C. 154(b) by 1162 days.

(21) Appl. No.: 10/477,386

(22) PCT Filed: Apr. 15, 2002

(86) PCT No.: PCT/SG02/00061
§ 371 (c)(1),
(2), (4) Date: May 17, 2004

(87) PCT Pub. No.: WO02/089970
PCT Pub. Date: Nov. 14, 2002

(65) Prior Publication Data
US 2004/0191319 A1    Sep. 30, 2004

(30) Foreign Application Priority Data
May 9, 2001    (SG) .............................. 200102700-2

(51) Int. Cl.
*A61K 9/14* (2006.01)
*A61K 9/00* (2006.01)
*B29B 9/00* (2006.01)
(52) U.S. Cl. ............................ 424/489; 424/400; 264/5
(58) Field of Classification Search ................ 424/400, 424/489; 264/5
See application file for complete search history.

(56) References Cited

U.S. PATENT DOCUMENTS

| 4,282,209 A | * | 8/1981 | Tocker ........................ 514/477 |
| 5,510,118 A | * | 4/1996 | Bosch et al. ................. 424/489 |
| 5,622,657 A | * | 4/1997 | Takada et al. ............... 264/4.32 |

FOREIGN PATENT DOCUMENTS

| WO | WO 00/18371 | * | 4/2000 |
| WO | WO 01/14036 A1 | * | 3/2001 |

* cited by examiner

*Primary Examiner*—Robert A Wax
*Assistant Examiner*—Aradhana Sasan
(74) *Attorney, Agent, or Firm*—Blakely, Sokoloff, Taylor & Zafman (57) ABSTRACT

A process for the production of a microparticle or a nanoparticle of a chemical compound comprising the steps of providing a solution of said chemical compound in a first liquid; providing a second liquid in which said chemical compound is insoluble or substantially insoluble; combining said liquids in a region of high shear thereby causing formation of said particles; and isolating said particles of said compound. The processing time of a coacervation style process can be reduced and the yield can be substantially increased both by control of the precipitation step which allows for desolvation step to be dispensed with leading to significant process time reduction. The invention also provides a molecular mixing unit comprising an outer body defining a mixing zone; a shear means to provide shear liquid in said mixing zone; at least one fluid inlet means for a first liquid; at least one fluid inlet means for a second liquid and a fluid outlet means.

18 Claims, 3 Drawing Sheets

PROCESS FOR THE CONTROLLED PRODUCTION OF ORGANIC PARTICLES

FIELD OF THE INVENTION

In general this invention relates to a process for the controlled production or organic micro-particles or nanoparticles which are useful in pharmaceutical applications and an apparatus for producing the same. In particular the present invention relates to a process and an apparatus for the production of organic drug particles of the nanoparticles size. These particles have been found to be particularly useful in the pharmaceutical industry as nanoparticles have useful drug release properties which in many applications are found to be superior to larger particles.

BACKGROUND OF THE INVENTION

The control of drug particle size is an important factor to be considered when producing a pharmaceutical formulation containing a solid active agent. For example, in certain applications microparticles are preferred whereas nanoparticles are preferred for other applications.

Nanoparticles for example have found increasing use in the pharmaceutical industry in recent years due to the inherent properties brought about by their high surface area to volume ratio. Accordingly, the ability of drug manufacturers to produce such fine drug powders for use in formulations with controlled particle size distribution has been an area of significant interest to in the pharmaceutical industry. Indeed a significant amount of the growth in the use of nanoparticles is due to the fact that the particle size distribution of the active ingredient in drug formulations has been found to have a direct influence on the release properties of the drug upon administration (especially oral administration).

In recent years, therefore, in addition to the interest in controlling drug particle size there has been significant interest in reducing the size of drug powders from the conventional micron-size range to the nano-size range in order to take advantage of this property. In addition, nanonization of pharmaceutical powders has been found to be beneficial for and applicable to a wide variety of drug delivery methodologies, such as colloidal, intravenous injection, inhalation, and oral drug delivery systems.

One example of such an application is that it has been found that reducing the particle size of a drug can enhance the dissolution of the drug into the biological environment. Thus it has been found that the chiral nonsteroidal anti-inflammatory drug, racemic ibuprofen—(often prescribed to treat arthritis, fevers, menstrual symptoms, and pain)—has a poor dissolution rate in water. Accordingly, improving its effectiveness in terms of increasing the dissolution rate in the biological environment can minimize the required intake of the drug by the patient. This in turn minimises both the cost to the patient and the chance of undesired side effects developing. This can be achieved by increasing the available surface area of ibuprofen (which is exposed to the biological environment) through reduction of the particle size from the micrometer to the nanometer range.

Reduction in particle size can also improve the penetration and dosage control of inhalation drug formulations. The lung tissue of a patient is an effective media for drug delivery owing to its large surface area. Insulin, for example, has been shown to be effectively transported by means of inhalation as early as the 1970s. This mode of transport is particularly desirable to diabetes sufferers as it can provide an alternative to daily multiple subcutaneous injections which can be undesirable. The use of nanoparticles in these applications is beneficial as nanoparticles are easier for the patient to inhale and, in addition, are less likely to cause irritation to the respiratory tract.

The benefits of being able to control drug particles size and in particular to control drug particles in the nanoparticle range is therefore manifest. There is therefore a need to develop improved methods to produce nanoparticles suitable for drug delivery applications.

One technique for the preparation of nanoparticles which has been used for protein particles is coacervation, which is the controlled desolvation from a solvent system. In comparison to the suspension cross-linking method, coacervation is considerably simpler. In the coacervation method, the solute is first dissolved into a solvent with or without the presence of a stabilizing agent (for example albumin in aqueous solution), then a coacervation agent (for example, ethanol) is added to the protein containing solution, with constant stirring, to precipitate the protein and form a suspension. The coacervation agent is subsequently evaporated from the suspension by heating the suspension slowly over an extended period of time (usually over 24 hours). As the coacervation agent slowly evaporates from the suspension, the precipitate will start to be re-dissolved back into the solvent, reducing the particle size of the remaining precipitate during the course of the desolvation process. It can therefore be seen that controlling the desolvation process can control the size of the particles produced leading to a number of particle sizes being achievable.

Unfortunately, the coacervation method suffers not only from the lengthy processing time required but also provides a low process yield as a significant amount of the desired solute is re-dissolved back into the solvent prior to the desired particle size being achieved. Whilst the material obtained can be re-subjected to the process this requires further time and energy input. In addition, the precipitate that is formed tends to be unstable and form aggregates which are undesirable from and end-user standpoint. It is clear therefore that viable alternatives/improvements to this method are required.

INFORMATION DISCLOSURE

U.S. Pat. No. 6,007,791 in the name of Chiron Corporation describes a process of preparing microspheres, films and coatings from proteins or modified proteins in which the protein product is stabilized by carrying out the preparation of the microspheres in the presence of an aqueous solution of at least one α-hydroxy acid. This uses the α-hydroxy acid as a stabilising agent for the microspheres. The methods of coacervation described in this practice standard coacervation methodology with an aqueous solution of the protein to be converted into a microsphere with a coacervation agent stirring the mixture to form microspheres. The difficulty with such a process is as noted that microspheres produced normally in the 10-50 micrometer range and instead of the nanometer range.

U.S. Pat. No. 5,879,715 in the name of CeraMem Corporation relates to a process for the production of inorganic nanoparticles by precipitating the inorganic nanoparticles by a precipitating agent from a microemulsion with a continuous and a non-continuous phase; and concentrating the precipitated nanoparticles employing an ultrafiltration membrane. In essence this technology utilises standard coacervation techniques.

U.S. Pat. No. 5,916,596 in the name of Vivorx Pharmaceuticals, Inc. relates to a process for producing nanoparticles using standard coacervation techniques wherein the particle size is controlled by careful solvent selection and preparation conditions. There is no teaching in this document of the use of high shear in the coacervation step leads to control particle size.

U.S. Pat. No. 5,874,029 in the name of The University of Kansas describes production of microparticles and nanoparticles in which a compressed fluid and a solution including a solvent and a solute are introduced into a nozzle to produce a mixture. The mixture is then passed out of the nozzle to produce a spray of atomized droplets. The atomized droplets are then contacted with a supercritical antisolvent to cause depletion of the solvent in the droplets so that the particles are produced from the solute. Preferably, these particles have an average diameter of 0.6 μm or less. This therefore relies on a spraying type vaporisation process.

Whilst all these prior art documents relate to coacervation or a variation thereof, they all control the particle size by standard coacervation technology such as judicious solvent selection and/or other physical steps. It is typically found that these variables are very compound specific and therefore the methods disclosed are not methods that can be utilised for all compounds. In addition, as noted above, many of these compounds or methods only produce microparticles and do not produce particles in the nanoparticle range.

In the present invention, a novel technique has been developed to reduce the processing time of a coacervation style process and, in addition, substantially increase the yield. This has been achieved in the present process by control of the precipitation step which allows for the desolvation step to be dispensed with leading to significant process time reduction. In addition, utilising the present process it is typically found that higher process yields are obtained.

SUMMARY OF THE INVENTION

In one aspect the present invention provides a process for the production of a microparticle or a nanoparticle of a chemical compound comprising:
 (a) providing a solution of said chemical compound in a first liquid;
 (b) providing a second liquid in which said chemical compound is insoluble or substantially insoluble;
 (c) combining said liquids in a region of high shear thereby causing formation of said particles; and
 (d) isolating said particles of said compound.

Preferably the process of combined the liquids in a region of high shear is achieved by injecting said liquids into a mixing zone containing a shear means. Preferably the injection is carried out at a high injection velocity of >1 ms$^{-1}$ more preferably >3 ms$^{-1}$ most preferably >5 ms$^{-1}$. It is also preferred that the high shear is provided by rapid rotation of the shear means in the mixing zone leading to shearing of liquids in said mixing zone.

In yet a further aspect the invention provides a molecular mixing unit comprising:
 (a) an outer body defining a mixing zone;
 (b) a shear means to provide shear to said mixing zone;
 (c) at least one fluid inlet means for a first liquid;
 (d) at least one fluid inlet means for a second liquid;
 (e) a fluid outlet means.

By the use of this unit the precipitation step can be controlled as the unit allows control of the step of adding the coacervation agent (second liquid) to the solute-laden solvent (first liquid) to control the nucleation and particle growth. The particle size can be controlled in either micron or nano size region by adjusting the rotational speed of the shear means in the mixing zone, by different structural features of the shear means and injecting shear of first and second liquids into the mixing zone at different rates of injection.

DETAILED DESCRIPTION OF THE FIGURES

DETAILED DESCRIPTION OF THE INVENTION

As used herein nanoparticles mean particles having an average particle size of less than 100 nanometers.

As used herein microparticles mean particles having an average particle size of less than 100 micrometers.

As used herein nanonization means the process of reducing the particles to be in a range such that the average particle size is less than 1000 nanometers in size preferably less than 100 nanometers in size.

In conventional coacervation methods, high speed stirring is used to disperse the precipitate that is formed during the mixing of the coacervation agent and solvent. It has been found, however, that stirring on its own has little or no control on the nucleation and the growth of the particles during the precipitation process. Accordingly, particles formed during the initial precipitation in conventional coacervation methods are typically large and irregular, and subsequently, require a lengthy desolvation step to reduce the size of the particle to the desired nanoparticle range.

After significant research the present inventors have found that if during the precipitation step the fluids are subject to a shearing means to impart sufficiently high shear to the liquids either as they are combined or immediately thereafter the particle size can be controlled. Whilst not wishing to be bound by theory it is thought subjection of the liquids to high shear leads to improved interaction between the two liquids leading to faster precipitation of the desired compound caused by the mixing. This is thought to occur as the high shear breaks the two liquids up into smaller particles and leads to more intimate mixing between the two liquids and hence more homogeneous precipitation of the drug particles. This thus increases the rate at which the liquids interact in turn increasing the speed of precipitation of the chemical compound from solution. As will be clear to a skilled addressee the quicker the homogeneous mixing of the two liquids and the faster the precipitation process, the smaller and the more uniform the particles produced during precipitation will be.

Fast precipitation alone results in big particles and the applicants have found that you need quick homogeneous mixing to ensure that the shear will break up the liquid into nanosized droplets, which in turn will result in the precipitation of a nanosized particle. Once again, without wishing to be bound by theory it is thought that in such precipitation reactions between the two liquids all or substantially all the dissolved solid in a drop of solvent will precipitate when brought into contact with a precipitating solvent. Accordingly, following this theory the smaller the droplets can be made when this occurs the smaller the particles of drug formed will be. In addition it is expected that the quicker the homogeneous mixing and the faster the precipitation leads to a more uniform particle size distribution observed. This of course will be clearly desirable as it ensures more uniformity of activity of the drug in use.

In the process of the invention it is preferred that the shearing means is a specially designed packing for mass transfer enhancement and micromixing intensification. This use of a shearing means significantly increases the intensity of micromixing between the solvent and coacervation agent (first and second liquids), therefore, controlling the nucleation and the growth of the particles right from the start of the precipitation step. In many cases, fine particles of less than 200 nm can be formed instantaneously after the second liquid is added to the first liquid with no further desolvation step required which differentiates the present process from previous processes. This therefore significantly reduces the processing time required and increases the product yield. The process will now be discussed in greater detail.

(a) Chemical Compounds

The process of the present invention can be utilised with a number of chemical compounds. Indeed, in principle the process can be carried out with any chemical compound however the compound must be such that it is able to withstand subjection to the high shear encountered in the process without degradation. As such some polymeric compounds may not be amenable to the process of the invention nor may some particularly sensitive long chain proteins. It is expected, however that a skilled addressee would be quickly able to determine the suitability of a compound to subjection to the process. In addition, in order to be subjected to this process the compound must be soluble in at least one solvent. This restriction typically presents no problem as most compounds are typically soluble in at least one solvent as would be clear to a skilled addressee. It is preferred that the compound is an organic compound particularly an organic drug compound.

The compound used may preferably be selected from any one of the following:

Antacids, antibiotics, anti-inflammatory substances, coronary dilators, peripheral vasodilators, anti-infectives, psychotropics, anti-manics, stimulants, anti-histamines, laxatives, decongestants, vitamins, gastro-intestinal sedatives, anti-diarrhoeal preparations, anti-anginal drugs, vasodilators, anti-arrhythmics, anti-hypertensive drugs, vasoconstrictors and migraine treatments, anti-coagulants and anti-thrombotic drugs, analgesics, anti-pyretics, hypnotics, sedatives, anti-emetics, anti-nauseates, anti-convulsants, neuromuscular drugs, hyper- and hypoglycaemic agents, thyroid and anti-thyroid preparations, diuretics, anti-spasmodics, uterine relaxants, mineral and nutritional additives, anti-obesity drugs, anabolic drugs, erythropoietic drugs, anti-asthmatics, bronchodilators, expectorants, cough suppressants, mucolytics, anti-ulcer and anti-urecemic drugs;

Gastro-intestinal sedatives such as metoclopramide and propantheline bromide, Antacids such as aluminium trisilicate, aluminium hydroxide and cimetidine, Antibiotics such as cefradine and amoxycillin;

Anti-inflammatory drugs such as phenylbutazone, indomethicin, naproxen, ibuprofen, flurbiprofen, diclofenac, dexamethasone, prednisone, and prednisone;

Coronary vasodilator drugs such as glyceryl trinitrate, isosorbide dinitrate and pentaerythritol tetranitrate, peripheral;

Cerebral vasodilators such as soloctidilum, vincamine, naftidrofuryl oxalate, co-dergocrine mesylate, cylandelate, papaverine and nicotine acid;

Anti-infective substances such as 1-Napthyl Salicylate, erythromycin stearate, cephalexin, nalidixic acid, tetracycline hydrochloride, ampicillin, flucloxacillin sodium, hexamine mandelate hexamine hippurate, and amoxacylin vancomycin;

Neuroleptic drugs such as flurazepam, diasepam, temazepam, amitryptyline, doxepin, lithium carbonate, lithium sulfate, chlorpromazine, thioridazine, trifluperazine, fluphenazine, piperothiazine, haloperidol, maprotiline hydrochloride, imipramine and desmethylimipramine;

Central nervous stimulants such as methylphenidate, ephedrine, epinephrine, isoproterenol, amphetamine sulfate and amphetamine hydrochloride;

Antihistamic drugs such as diphenhydramine, diphenylpyraline, chlorpheniramine and brompheniramine;

Anti-diarrheal drugs such as bisacodyl and magnesium hydroxide, the laxative drug, dioctyl sodium sulfosuccinate;

Nutritional supplements such as ascorbic acid, alpha tocopherol, thiamine and pyridoxine;

Anti-virals such as acyclovir;

Anti-spasmodic drugs such as dicyclomine and diphenoxylate, drugs affecting the rhythm of the heart such as verapamil, nifedipine, diltiazem, procainamide, disopyramide, bretylium tosylate, quinidine sulfate and quinidine gluconate;

Drugs used in the treatment of hypertension such as propranolol hydrochloride, guanethidine monosulphate, methyidopa, oxprenolol hydrochloride, captopril and hydralazine;

Drugs used in the treatment of migraine such as ergotamine;

Drugs affecting coagulability of blood such as epsilon aminocaproic acid and protamine sulfate;

Analgesic drugs such as acetylsalicylic acid, acetaminophen, codeine phosphate, codeine sulfate, oxycodone, dihydrocodeine tartrate, oxycodeinone, morphine, heron, nalbuphine, butorphanol tartrate, pentazocine hydrochloride, cyclazacine, pethidine, buprenorphine, scopolamine and mefenamic acid;

Anti-epileptic drugs such as phenytoin sodium and sodium valproate;

Neuromuscular drugs such as dantrolene sodium;

Substances used in the treatment of diabetes such as tolbutamide, disbenase glucagon insulin and metformin;

Drugs used in the treatment of thyroid gland dysfunction such as triiodothyronine, thyroxine and propylthiouracil;

Diuretic drugs such as furosemide, chlorthalidone, hydrochlorthiazide, spironolactone and trimterone, the uterine relaxant drug ritodrine;

Appetite suppressants such as fenfluramine hydrochloride, phentermine and diethylproprion hydrochloride;

Anti-asthmatic and bronchodilator drugs such as aminophylline, theophylline, salbutamol, orciprenaline sulphate and terbutaline sulphate;

Expectorant drugs such as guaiphenesin, cough suppressants such as dextromethorphan and noscapine;

Mucolytic drugs such as carbocisteine;

Anti-septics such as cetylpyridinium chloride, tyrothricin and chlorhexidine;

Decongestant drugs such as phenylpropanolamine and pseudoephedrine, hypnotic drugs such as dichloralphenazone and nitrazepam;

Anti-nauseant drugs such as promethazine theoclate;

Haemopoietic drugs such as ferrous sulphate, folic acid and calcium gluconate; and Uricosuric drugs such as sulphinpyrazone, allopurinol and probenecid. The choice of chemical compound to be converted to a particle will determine the first and second liquids to be used in the process of the invention.

(b) First and Second Liquids

The selection of first and second liquids is a very important step in the process of the invention. The first and second liquids can be single solvents or mixtures of solvents however there are a number of features that the liquids must have in order to successfully practice the invention. It is important for example, that the first liquid is one in which the compound to be converted to a particle is soluble. Whilst this will clearly vary depending on the particular compound the choice of a first liquid will typically not cause difficulty for a skilled addressee as the solubility can be determined easily by trial and error. It is particularly preferred that the first solvent is water as this is most environmentally friendly and cost effective.

Once the first liquid has been selected the compound is then dissolved in the liquid. In principle the amount of first liquid used is irrelevant as long as there is an adequate amount to fully dissolve the compound to provide a solution of the compound in the first liquid. In practical terms, however, for the purposes of economy it is found that the amount of first solvent should be no more than is necessary to just dissolve the compound (ie just enough to produce a saturated solution of the compound in the first liquid). It is found that if an excess of liquid is used the yield of recovered particles from the process of the invention is lower and/or a larger amount of second liquid is required to achieve a comparable yield. In both instances from an economic standpoint this is undesirable and therefore excess amounts of the first liquid should be avoided where possible.

The second liquid should generally be chosen such that the compound to be converted to a particle is insoluble or substantially insoluble in the second liquid. Alternatively the second liquid is chosen so that it is one in which when it is brought into contact with a solution of the compound in the first liquid leads to precipitation of the chemical compound from solution. It is preferable that the second liquid is miscible with the first liquid although this need not be the case. It is particularly preferred that the second liquid is ethanol.

The ratio of first liquid to second liquid used in the process of the invention can vary greatly although it is preferred that the ratio is near to one. Accordingly in a preferred ratio the first and second liquids are utilised in a ratio of from 10:1 to 1:10, more preferably 4:1 to 1:4, even more preferably from 3:1 to 1:3, yet even more preferably from 0.8:1 to 1.2:1.0, most preferably 1:1. The exact ratio will depend on the chemical compound selected and the liquids chosen. A skilled addressee will understand that any number of ratios will work successfully for any given combination of chemical compound, first and second liquid.

(c) Formation of an Intimate Mixture

Once the liquids have been chosen they are combined in a region of high shear to form an intimate mixture of the two liquids thereby causing precipitation of particles of the compound from the mixture. A preferred method of combining the liquids is to inject them into a mixing zone containing a shear means. In a particularly preferred embodiment the shear means is rotating in the mixing zone and said first and said second liquids are injected directly onto the rotating shear means.

Preferably the liquids are injected simultaneously through separate inlets. In an even more preferred embodiment the liquids are each injected via a plurality of inlets. The inlets can be located either around the outside of the mixing zone or are located so as to deliver the liquids to the centre of the mixing zone. In a particularly preferred embodiment the liquids are injected through a distributor located in the centre of the mixing region surrounded by the rotating shear means. The injection velocity of the liquid (flow velocity as it exists from the inlet) is preferably greater 1 $ms^{-1}$, more preferably greater than 3 $ms^{-1}$ and most preferably greater than 5 $ms^{-1}$.

(d) Shear

The process involves the use of a shear means to impart high shear to the two liquids in the mixing zone. This has the advantage that the two liquids are adequately mixed to form an intimate mixture leading to the formation of a precipitate of the desired size. The shear means is preferably a packing with a surface area of 200-3000 $m^2/m^3$. The packing can be such that it is structured packing or random packing. A preferred packing is a packing of the wire mesh type packing that can be made from either stainless steel, plain metal alloy, titanium metal or plastic. It is preferred that the packing is a substantially cylindrical shear means formed from at least one mesh layer. More preferably it is formed from a plurality of overlapping mesh layers. In a most preferred embodiment the shear means is formed by rolling mesh to form a cylindrical shear means wherein the cylindrical section has sides formed by a plurality of overlapping mesh layers. If it is used it is preferred that the mesh has a mesh size of 0.05 to 3 mm, more preferably 0.1 to 0.5 mm. The mesh has a preferred mesh porosity of at least 90%, preferably more than 95%.

In a particularly preferred embodiment the shear means is mounted on a shaft in the mixing zone and rotates in the mixing zone. In a particularly preferred embodiment the shear means is a cylindrical shape and defines a hollow to accommodate the inlets for the liquids. It will be appreciated, however, that the shape of the container in which the two liquids are combined can also be used to impart shear to the liquids.

As discussed about it is preferred that the shear means rotates in said mixing zone at a sufficient speed to input high shear to said liquids in said zones. The rotation speed is typically of the order of 100 to 15000 rpm, preferably 500 to 12000 rpm, even most preferably 5000 to 8000 rpm. The use of such a strong rotation of the shear means ensures that the two liquids in the mixing zone are subjected to strong shear immediately upon injection.

In the process of the invention it is preferred that the liquids are injected into the mixing region by way of a liquid distributor located in the centre of the mixing region in a hollow defined by the rotating shear means. It is preferred that the liquids are injected directly onto the shear means and have an injection speed of at least 1 $ms^{-1}$, more preferably at least 3 $ms^{-1}$, most preferably at least 5 $ms^{-1}$. It is preferred that each of the liquids is injected through a plurality of the inlets. It is preferred that each inlet for the first inlet is spaced no further than 15° of are from an inlet for the second outlet.

(e) Isolation

Once the liquids have been mixed and the particles produced the mixture is discharged from the mixing zone and the particles isolated. If the process is carried out as a continuous process which is preferred the addressed liquids are constantly being withdrawn from the mixing zone and the solid isolated. The particles may be isolated by filtration, centrifugation or any other method of isolation of a solid from a liquid. It is preferred that the solid is isolated by filtration.

A variety of drug and organic nanoparticles can be prepared using the above method. In addition, the active ingredients can also be co-precipitated with polymer to form drug encapsulated polymer nanospheres or microspheres. Examples of polymers that can be used in this way are Polyisobutylcyanoacrylate (PIBCA), (2) Polyisohexlcyanoacrylate (PHICA), Poly (D-L lactic acid) (PLA) and Polystyrene (PS).

In the embodiment described above the process has been described as a continuous process in a specific reaction vessel. It is to be understood, however, that the process could be carried out in a continuous fashion using a pipe means as the reactor. For example the process could be such that the shear means is located in a pipe and the two fluids are injected into the pipe with the pressure of the liquids forcing the combined liquids through the shear means located in the pipe. The amount of shear could be controlled by the number of shear devices/means located in the pipe and the residence time of the liquids in the area of shear. In the method there would be no requirement to rotate the shear means.

Description of the Molecular Mixing Unit

In yet a further aspect, the invention provides a molecular mixing unit comprising:
 (a) an outer body defining a mixing zone;
 (b) a shear means to provide shear liquids in said mixing zone;
 (c) at least one fluid inlet means for a first liquid;
 (d) at least one fluid inlet means for a second liquid;
 (e) a fluid outlet means.

The outer body of the molecular mixing unit can be made of a number of materials. It is preferred that the body is made of stainless steel. The body is designed such that it defines a mixing zone. The mixing zone can in theory be any of a number of sizes and the size chosen will depend of the rate of the process to be carried out and the amount of material to be processed.

The mixing zone is provided with a shear means located within said mixing zone to impart high shear to said liquids injected into said mixing zone. In principal, the shear means can be any device which imparts high shear on fluid. In the preferred embodiment the shear means is a molecular packing with a surface area of 200 to 3000 $m^2/m^3$. The packing can be either structured packing or random packing with structured packing being particularly preferred. The preferred packing is packing of wire mesh type that can be made of either stainless steel, plain metal alloy, titanium or plastic. It is preferred that the packing is a substantially cylindrical shear means formed from at least one mesh layer. More preferably it is formed from a plurality of overlapping mesh layers. In a most preferred embodiment the shear means is formed by rolling mesh to form a cylindrical shear means wherein the cylindrical section has sides formed by a plurality of overlapping mesh layers. It is preferred that the mesh of this packing has a mesh size of 0.05 to 3 mm, preferably 0.1 to 0.5 mm.

In a particularly preferred embodiment of the invention the shear means is a molecular packing attached to a rotating means located in said mixing zone to rotate said shear means in the mixing region. In such an embodiment as the rotating means rotates said packing rotates imparting high shear onto the injected liquids. It is preferred that said shear means also defines a hollow into which the liquid inlets can be located. Whilst not wishing to be bound by theory it is felt that the use of a high shear device in the unit breaks the solution into discrete particles of the two liquids leading to high surface area contact between them leading to the fast precipitation and formation of the desired particles.

It is found to be particularly efficient if the two liquids are injected into the mixing zone via separate fluid inlets. Accordingly, preferably the molecular mixing device has at least one fluid inlet for fluid inflow of each of the first and second liquids respectively. Preferably there are a plurality of inlets for each liquid. Of course, these liquid inlets may be arranged in a number of ways depending on the structural design of the mixer. It is preferred that the liquid inlets are located in a distributor which preferably is located in the hollow defined by said shear means. Preferably the distributor defines a plurality of inlets for each of the first and second liquids. In a most preferred embodiment the liquid inlets alternate on the distributor.

In addition, there should be at least one liquid outlet means for draining the molecular mixing device either in a batchwise or continuous fashion. The molecular mixing device will now be described in greater detail with reference to the attached FIG. 5.

Figure 5:
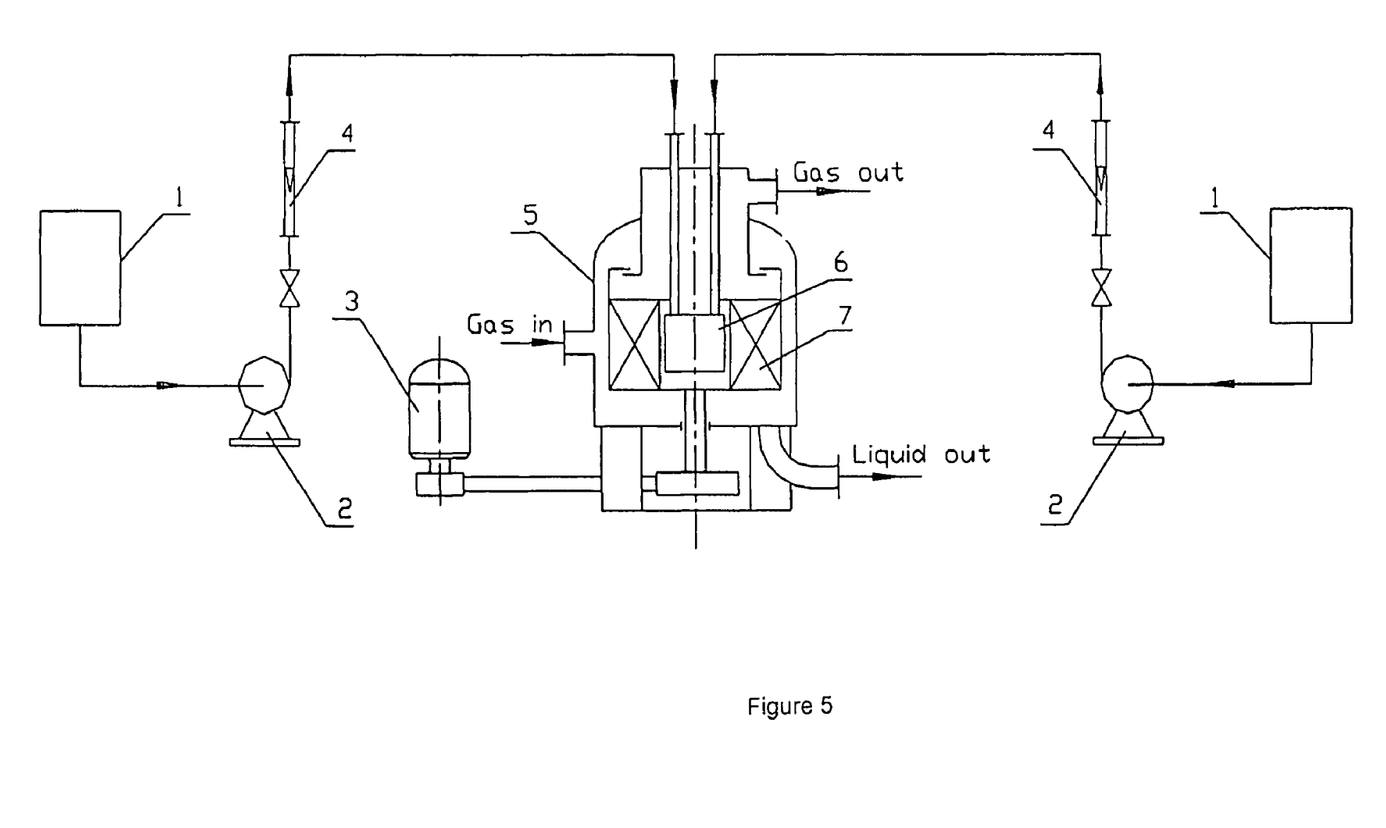
FIG. 5—This is a diagram showing one embodiment of the molecular mixing unit of the invention.

In the FIG. 5 the outer shell of a molecular mixing unit is shown (5). The outer shell shown here includes a gas blanket shown as gas-in and gas-out in order to isolate the reaction process from the oxygen environment. Whilst this is shown in a Figure this is merely a preferred embodiment as gas blanketing will not be required for a number of compounds. The first and second liquids are located separately in the solution chambers (1). For a typical run, one of the liquids would be located into chamber (1) on the left of the drawing and the other liquid would be located in solution chamber (1) on the right. These solutions are then pumped through pumps (2) to flow metres (4) through pipes into a distributor (6) located within the mixing chamber. This distributor is located within a hollow created by the shear means (7). The shear means is a cylindrical shear means which surrounds the distributor (6) forming a hollow in which the distributor sits. Shear means (7) is shown attached to shaft which in turn is attached to motor (3) in order to rotate the shear means within the mixing zones. In use the solutions are pumped in through the distributor in the mixing zone onto the rotating shear device. As will be understood by a skilled addressee there are a number of ways in which the liquids can be injected into the mixing zone and the one shown in this figure is merely a preferred embodiment. The number of inlet points for each liquid and the size and shape of the inlet points would depend on the compounds chosen and may vary greatly. The pump is rated so that the velocity of liquid pumped into mixing chamber through the inlet points should preferably be in the range of 1 $ms^{-1}$, more preferably at least 3 $ms^{-1}$. and most preferably greater than 5 $ms^{-1}$.

As will be appreciated by also a skilled addressee after a series of long processing, the packing may be clogged. As would be understood this can be easily remedied by washing with solvent materials and or by cleaning the packing dye by using conventional clean-in place solvent procedures.

The invention will now be described with reference to the following examples.

EXAMPLE 1

Preparation of 1-Napthyl Salicylate (NAS) Nanoparticles by the Molecular Mixing Method A 5% by weight NAS was dissolved in ethanol. The second liquid used was water. Water and the NAS/ethanol solution were injected into the molecular mixing unit continuously at a volumetric flow rate of 5 volume of water to 1 volume of NAS/ethanol solution. The two solutions were injected directly into the high speed rotational packing located inside the molecular mixing unit. The rotational speed was set at 10,000 rpm. The nanoparticles were recovered by sterile-filer and vacuum dried (it can also be freeze dried, spray dryer, flash dryer).

Figure 1:
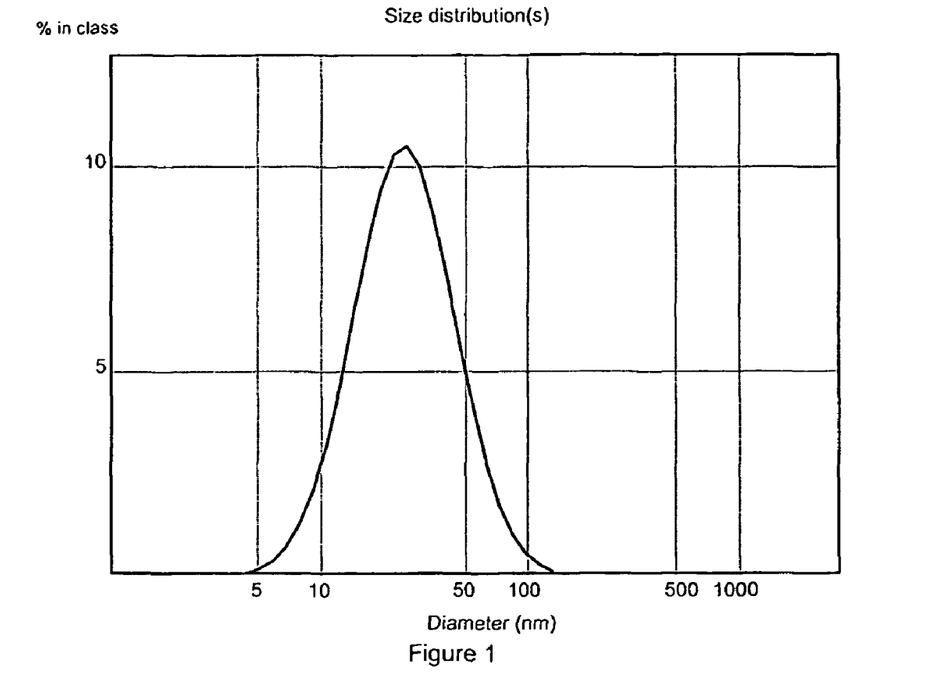
FIG. 1—This figure shows the particle size distribution obtained for the particles produced in example 1.

The particle size of the nanoparticles was analyzed by the PCS (Photon Correlation Spectrum, Particle Sizer, Malvern, UK) and was found to be 25.1 nm as shown in FIG. 1.

EXAMPLE 2

Same conditions as example 1 with the exception of rotational speed being reduced to 2500 rpm.

Figure 2:
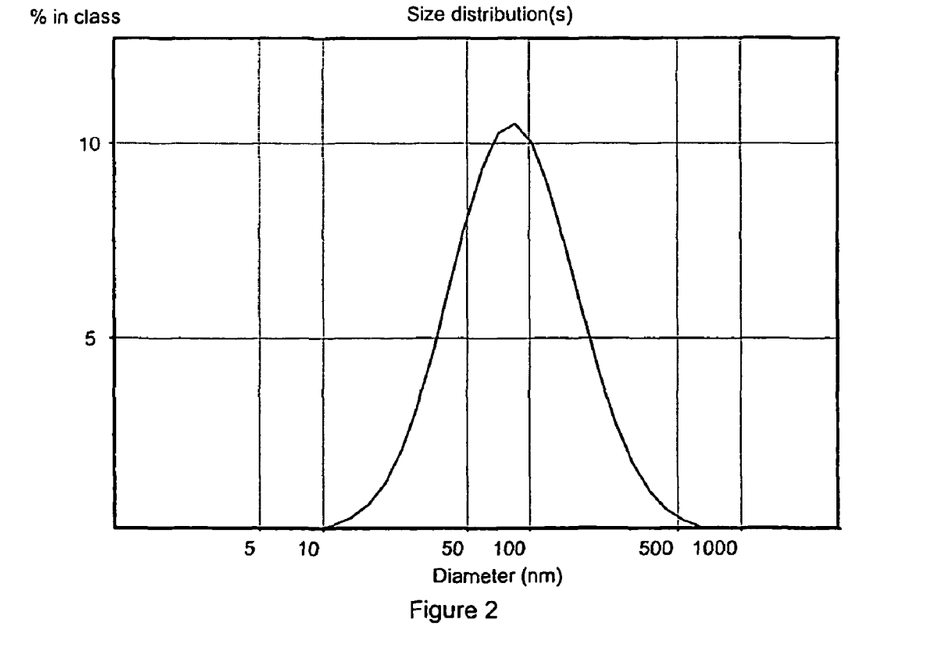
FIG. 2—This figure shows the particle size distribution obtained for the particles produced in example 2.

The particle size of the nanoparticles was analyzed by PCS and was found to be 82.3 nm as shown in FIG. 2.

EXAMPLE 3

Preparation of BSA Nanoparticles by the Molecular Mixing Method

A 5% by weight BSA aqueous solution was prepared. The second liquid used was ethanol. Ethanol and the BSA solution were injected into the molecular mixing unit continuously at a volumetric flow rate of 3 volume of ethanol to 1 volume of BSA solution. The two solutions were injected directly into the high speed rotational packing located inside the molecular mixing unit. The rotational speed was set at 5000 rpm. The nanoparticles were recovered by sterile-filer and vacuum dried (it can also be freeze dried, spray dryer, flash dryer).

Figure 3:
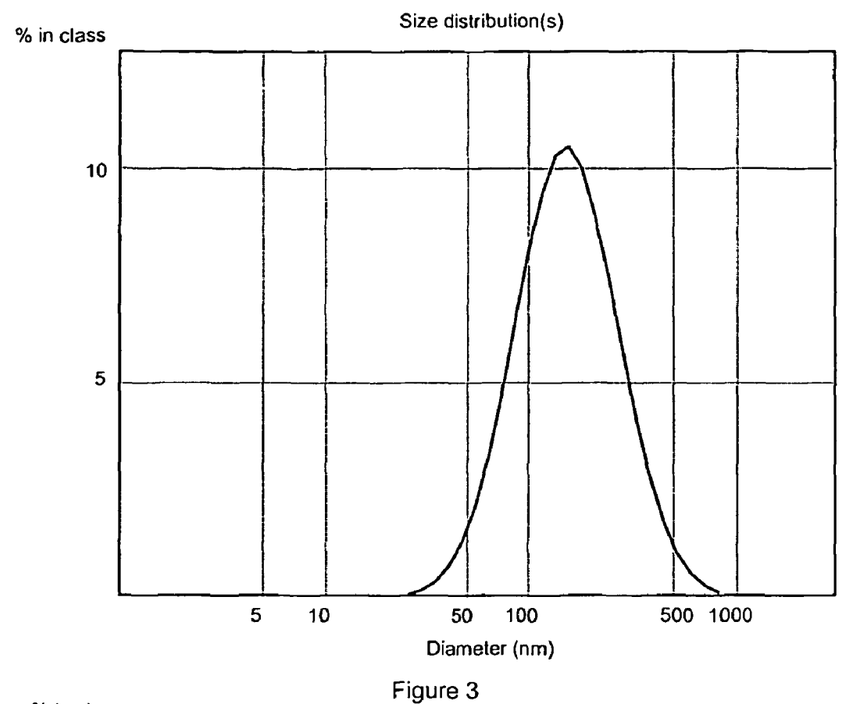
FIG. 3—This figure shows the particle size distribution obtained for the particles produced in example 3.

The particle size of the nanoparticles was analyzed by PCS and was found to be 151 nm as shown in FIG. 3.

EXAMPLE 4

Same condition as example 3 with the exception of solvent: anti-solvention volume ratio being reduced to 1:2.

Figure 4:
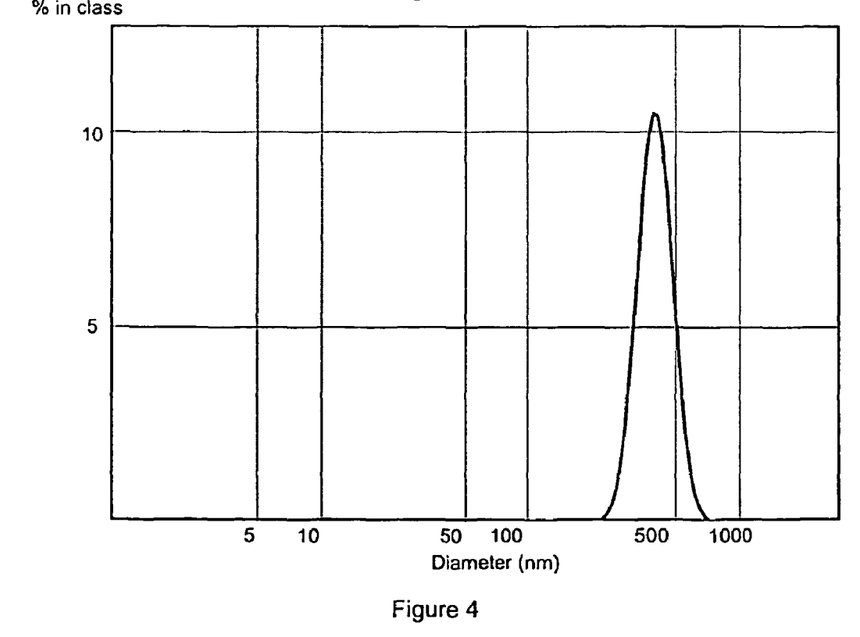
FIG. 4—This figure shows the particle size distribution obtained for the particles produced in example 4.

The particle size of the nanoparticles was analyzed by PCS and was found to be 400.9 nm as shown in FIG. 4.

The invention claimed is:

1. A process for the production of nano-sized particles of a drug compound, the process comprising the steps of:
   (a) providing a solution of said drug compound in a first liquid;
   (b) providing a second liquid in which said drug compound is insoluble, or substantially insoluble;
   (c) providing a molecular packing configured to rotate and induce a region of high rotational shear within a mixing zone; wherein said molecular packing is a substantially cylindrical shaped molecular packing formed from at least one mesh layer;
   (d) combining said first liquids and said second liquid directly onto the molecular packing to impart high rotational shear to said liquids during said combining, and wherein the high rotational shear forms discrete droplets of the first liquid and second liquid leading to high surface area contact therebetween, said high surface area contact of said droplets of the first liquid and second liquid causing precipitation and formation of said particles of the drug compound having a uniform particle size distribution;
   (e) controlling the uniform particle size of the drug particles to a particle size distribution wherein the median particle size is less than 500 nm and the maximum particle size is less than 1000 nm and wherein the particles are in the nano-size range by controlling the speed of rotation of the molecular packing within said mixing zone; and
   (f) isolating said nano-sized particles of said drug compound.

2. A process according to claim 1 wherein said step (c) comprises injecting said liquids into said mixing zone.

3. A process according to claim 2 wherein said liquids are injected into said mixing zone directly onto said molecular packing.

4. A process according to claim 1 wherein said molecular packing is rotating at a speed of from about 1,000 rpm to about 10,000 rpm.

5. A process according to claim 2 wherein said first iquid is water.

6. A process according to claim 5 wherein said second liquid is ethanol.

7. A process according to claim 6 wherein said first liquid and said second liquid are injected into said mixing zone at a ratio of 0.8:1 to 1.2:1.

8. A process according to claim 1 wherein said molecular packing is formed from a plurality of overlapping mesh layers.

9. A process according to claim 1 wherein said molecular packing is formed by rolling a mesh to form a substantially cylindrical shaped molecular packing, wherein said cylindrical section is defined by sides with a plurality of overlapping mesh layers.

10. A process according to claim 1 wherein said mesh has a mesh size of 0.5 to 3.0 mm.

11. A process according to claim 10 wherein said mesh has a mesh size of 0.1 to 0.5 mm.

12. A process according to claim 1 wherein said mesh has a porosity of greater than 90%.

13. A process according to claim 12 wherein said mesh has a porosity of greater than 95%.

14. A process according to claim 2 wherein each of said liquids are injected into said mixing zone through a plurality of inlets.

15. A process according to claim 14 wherein each inlet for said first liquid is located within said mixing zone no further than 15 degree of arc from an inlet for said second liquid.

16. A process according to claim 3 wherein said injection velocity of said injected liquids is greater than 1 ms$^{-1}$.

17. A process according to claim 3 wherein said injected liquids have an injection velocity of greater than 3 ms$^{-1}$.

18. A process according to claim 3 wherein said injected liquids have an injection velocity of greater than 5 ms$^{-1}$.

* * * * *

UNITED STATES PATENT AND TRADEMARK OFFICE
CERTIFICATE OF CORRECTION

| | | |
|---|---|---|
| PATENT NO. | : 7,875,295 B2 | |
| APPLICATION NO. | : 10/477386 | |
| DATED | : January 25, 2011 | |
| INVENTOR(S) | : Sung Lai Jimmy Yun and Jian Feng Chen | |

It is certified that error appears in the above-identified patent and that said Letters Patent is hereby corrected as shown below:

On the Title Page, Item (73) Assignee: delete "Singapore" insert -- Faber Heights --

Column 12, Claim 5, line 18, delete "iquid" insert -- liquid --

Signed and Sealed this
Tenth Day of May, 2011

David J. Kappos
*Director of the United States Patent and Trademark Office*